US00PP18820P2

(12) United States Plant Patent
Kunhardt

(10) Patent No.: US PP18,820 P2
(45) Date of Patent: May 20, 2008

(54) ***ANISODONTEA* PLANT NAMED 'CEFDONPIN'**

(50) Latin Name: *Anisodontea elegans*
Varietal Denomination: Cefdonpin

(75) Inventor: Linda Elin Noack Kunhardt, Beacon Bay (ZA)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 11/509,542

(22) Filed: Aug. 24, 2006

(51) Int. Cl.
*A01H 5/00* (2006.01)

(52) U.S. Cl. ..... Plt./263

(58) Field of Classification Search ..... Plt./226
See application file for complete search history.

(56) References Cited

PUBLICATIONS

UPOV–ROM GTITM, Plant Variety Database, 2007/02, GTI Jouve Retrieval Software, citation for 'CEFDONPIN'.*

* cited by examiner

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Anisodontea* plant named 'Cefdonpin', characterized by its upright and columnar plant habit; strong root system; freely flowering habit; large bright pink-colored flowers; and long flowering period.

1 Drawing Sheet

Botanical designation: *Anisodontea elegans.*
Cultivar denomination: 'Cefdonpin'.

BACKGROUND OF THE INVENTION

The present invention relates to a new and distinct cultivar of Anisodontea, botanically known as *Anisodontea elegans,* and hereinafter referred to by the name 'Cefdonpin'.

The new *Anisodontea* is a product of a planned breeding program conducted by the Inventor in Beacon Bay, South Africa The objective of the breeding program is to create new freely-flowering *Anisodontea* cultivars with a strong roots and long flowering season.

The new *Anisodontea* originated from a cross-pollination made by the Inventor in Beacon Bay, South Africa in 2001, of two unnamed selections of *Anisodontea* elegans, not patented. The cultivar Cefdonpin was discovered and selected by the Inventor as a flowering plant within the progeny of the stated cross-pollination in a controlled environment in Beacon Bay, South Africa in 2002.

Asexual reproduction of the new *Anisodontea* by terminal cuttings in a controlled environment in Beacon Bay, South Africa since 2002, has shown that the unique features of this new *Anisodontea* are stable and reproduced true to type in successive generations.

SUMMARY OF THE INVENTION

The cultivar Cefdonpin has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Cefdonpin'. These characteristics in combination distinguish 'Cefdonpin' as a new and distinct cultivar of *Anisodontea:*

1. Upright and columnar plant habit.
2. Strong root system.
3. Freely flowering habit.
4. Large bright pink-colored flowers.
5. Long flowering period.

Plants of the new *Anisodontea* can be compared to plants of the parent selections. Plants of the new *Anisodontea* differ from plants of the parent selections:

1. Plants of the new *Anisodontea* have a more uniform plant habit than whereas plants of the parent selections.
2. Plants of the new *Anisodontea* have larger flowers than plants of the parent selections.
3. Plants of the new *Anisodontea* have brighter pink-colored flowers than plants of the parent selections.

Plants of the new *Anisodontea* can be compared to plants of the *Anisodontea elegans* cultivar Elegant Lady, disclosed in U.S. Plant Pat. No. 16,301. In side-by-side comparisons conducted in Beacon Bay, South Africa, plants of the new *Anisodontea* differed from plants of the cultivar Elegant Lady in the following characteristics:

1. Plants of the new *Anisodontea* had stronger roots than plants of the cultivar Elegant Lady.
2. Plants of the new *Anisodontea* had a more open plant habit than plants of the cultivar Elegant Lady.
3. Flowers of plants of the new *Anisodontea* and the cultivar Elegant Lady differed in flower color as plants of the cultivar Elegant Lady had light purple-colored flowers.

BRIEF DESCRIPTION OF THE PHOTOGRAPHS

The accompanying colored photographs illustrate the overall appearance of the new *Anisodontea,* showing the colors as true as it is reasonably possible to obtain in colored reproductions of this type. Colors in the photographs may differ slightly from the color values cited in the detailed botanical description which accurately describe the colors of the new *Anisodontea*.

The photograph at the bottom of the sheet comprises a side perspective view of a typical flowering plant of 'Cefdonpin' grown in a container.

The photograph at the top of the sheet comprises a close-up view of a typical flower of 'Cefdonpin'.

DETAILED BOTANICAL DESCRIPTION

The photographs and following observations, measurements and values describe plants grown in Bonsall, Calif. in 10-cm containers in polyethylene-covered greenhouses during the summer under conditions which closely approximate commercial production. During the production of the plants, day temperatures averaged 32° C., night temperatures averaged 21° C. and light levels averaged 4,5000 foot-candles. Plants were about two months old when the photographs and the description were taken. In the description, color references are made to The Royal Horticultural Society Colour Chart, 1995 Edition, except where general terms of ordinary dictionary significance are used.

Botanical classification: *Anisodontea elegans* cultivar Cefdonpin.

Parentage:

*Female, or seed, parent.*—Unnamed selection of *Anisodontea elegans,* not patented.

*Male or pollen parent.*—Unnamed selection of *Anisodontea elegans,* not patented.

Propagation:

*Type.*—By terminal cuttings.

*Time to initiate roots, summer.*—About 10 days at temperatures of 24° C. to 26° C.

*Time to initiate roots, winter.*—About 14 days at temperatures of 18° C. to 20° C.

*Time to develop roots.*—About eight weeks at temperatures.

*Root description.*—Strong, fibrous; white, close to 155D, in color.

*Rooting habit.*—Freely branching; moderately dense.

Plant description:

*Plant form and growth habit.*—Upright and columnar plant habit. Vigorous growth habit.

*Branching habit.*—Freely branching, usually about three lateral branches develop after removal of terminal apex.

*Plant height.*—About 30 cm.

*Plant diameter* (*area of spread*).—About 12 cm.

Lateral branch description:

*Length.*—About 27 cm.

*Diameter.*—About 2 mm.

*Internode length.*—About 4 cm.

*Texture.*—Pubescent.

*Color.*—146A.

Foliage description:

*Arrangement.*—Alternate, simple.

*Length.*—About 3.2 cm.

*Width.*—About 3.3 cm.

*Shape.*—Tri-lobed.

*Apex.*—Rounded.

*Base.*—Acute to obtuse.

*Margin.*—Slightly serrate.

*Texture, upper and lower surfaces.*—Mostly glabrous, minute pubescence along veins of lower surface.

*Venation pattern.*—Palmate; reticulate.

*Color.*—Developing foliage, upper and lower surfaces: 146A. Fully developed foliage, upper surface: 146A; venation, 146A. Fully developed foliage, lower surface: 147B; venation, 147B.

*Petiole.*—Length: About 1.3 cm. Diameter: About 1 mm. Texture, upper and lower surfaces: Minute pubescence. Color, upper and lower surfaces: 146A.

Flower description:

*Flower arrangement.*—Single axillary flowers. Freely flowering habit with usually about three or four open flowers per lateral branch. Flowers face mostly outwardly.

*Natural flowering season.*—Plants flower continuously throughout the summer in South Africa. Flowers last about four to five days on the plant. Flowers persistent.

*Flower diameter.*—About 3.4 cm.

*Flower length* (*height*).—About 2.2 cm.

*Flower bud.*—Length: About 1 cm. Diameter: About 9 mm. Shape: Elliptical. Color: 74C.

*Petals.*—Arrangement: Corolla consists of five petals in a single whorl. Length: About 1.7 cm. Width: At widest point, about 1.9 cm; at base, about 2.5 mm. Shape: Spatulate. Apex: Rounded. Base: Attenuate. Margin: Entire; slightly undulate. Texture, upper and lower surfaces: Smooth, glabrous, satiny. Color: When opening, upper surface: 73C to 73D. When opening, lower surface: 80C. Fully opened, upper surface: 80C; venation, 74A. Fully opened, lower surface: 80C; towards the base, 73D.

*Sepals.*—Appearance: Five sepals fused into a star-shaped calyx. Length: About 6 mm. Width: About 5 mm. Shape: Elliptical. Apex: Acute. Margin: Entire. Texture, upper and lower surfaces: Minute pubescence. Color, upper surface: 146B to 146C. Color, lower surface: 146A to 146B.

*Peduncles.*—Length: About 1.6 cm. Diameter: Less than 1 mm. Angle: About 45° from stem axis. Strength: Strong. Texture: Minute pubescence. Color: 146A.

*Reproductive organs.*—Androecium: Stamen number: About 30. Filament length: About 4 mm. Filament color: Close to 155D. Anther shape: Rounded. Anther length: About 1 mm. Anther color: 75D. Amount of pollen: Scarce. Pollen color: 160D. Gynoecium: Pistil length: About 1.3 cm. Style length: About 6 mm. Style color: 155D. Stigma appearance: Pointed. Stigma color: 74A. Ovary color: 155A.

*Seed/fruit.*—Seed and fruit production has not been observed.

Temperature tolerance: Plants of the new *Anisodontea* have been observed to tolerate temperatures from about 6° C. to about 40° C.

Pathogen/pest resistance: Plants of the new *Anisodontea* have not been shown to be resistant to pathogens and pests common to *Anisodontea*.

It is claimed:

1. A new and distinct *Anisodontea* plant named 'Cefdonpin' as illustrated and described.

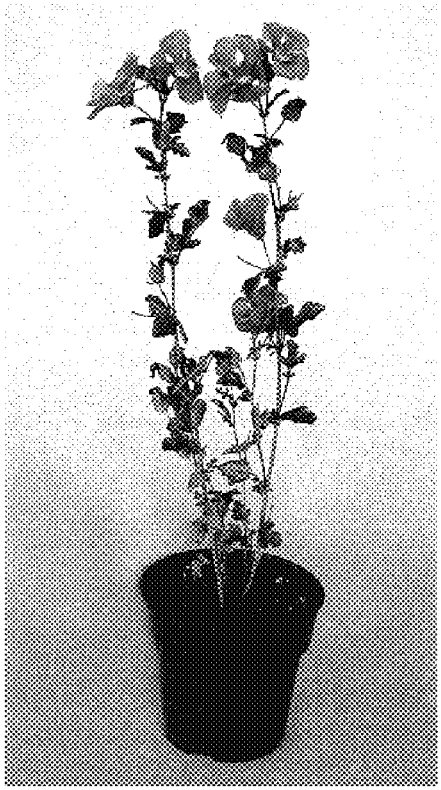
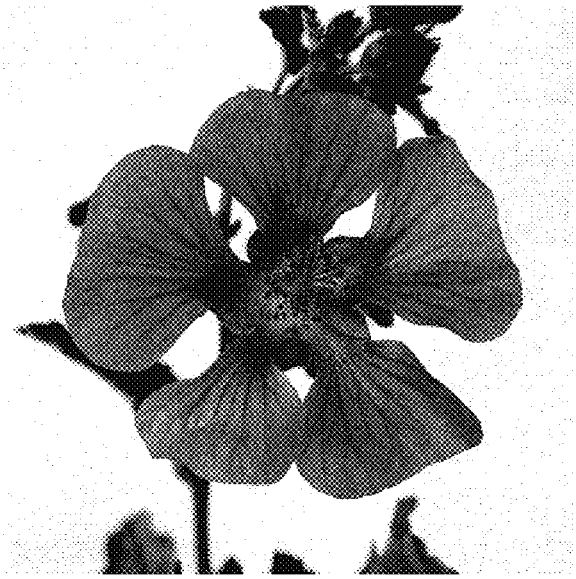

* * * * *